United States Patent [19]
Le et al.

[11] Patent Number: 5,489,719
[45] Date of Patent: Feb. 6, 1996

[54] PROCESS FOR THE PRODUCTION OF TERTIARY ALKYL ETHER RICH FCC GASOLINE

[75] Inventors: Quang N. Le, Cherry Hill; Robert T. Thomson, Lawrenceville, both of N.J.

[73] Assignee: Mobil Oil Corporation, Fairfax, Va.

[21] Appl. No.: 255,546

[22] Filed: Jun. 6, 1994

Related U.S. Application Data

[63] Continuation of Ser. No. 896,072, Jun. 2, 1992, abandoned.

[51] Int. Cl.$^6$ .......................... C07C 41/08; C07C 43/00; C07C 5/08; C07C 7/167
[52] U.S. Cl. ................ 585/261; 585/259; 568/688; 568/689; 568/697
[58] Field of Search ............. 44/444, 449; 568/697, 568/895, 899, 688, 689, 697; 585/259, 261

[56] References Cited

U.S. PATENT DOCUMENTS

| | | | |
|---|---|---|---|
| Re. 28,341 | 2/1975 | Wadlinger | 208/120 |
| 3,308,069 | 3/1967 | Wadlinger | 252/455 |
| 3,702,886 | 11/1972 | Argauer et al. | 423/328 |
| 4,016,218 | 4/1977 | Haag et al. | |
| 4,193,770 | 3/1980 | Chase et al. | 44/449 |
| 4,252,541 | 2/1981 | Herbstman | 44/449 |
| 4,330,679 | 5/1982 | Kohler | 568/697 |
| 4,361,422 | 11/1982 | Derrien et al. | 44/449 |
| 4,605,787 | 8/1986 | Chu | 568/697 |
| 4,714,787 | 12/1987 | Bell | 568/697 |
| 4,978,807 | 12/1990 | Smith et al. | 568/697 |
| 5,001,292 | 3/1991 | Harandi et al. | 44/449 |

FOREIGN PATENT DOCUMENTS

| | | |
|---|---|---|
| 0055045 | 6/1982 | European Pat. Off. . |
| 3813689A1 | of 0000 | Germany . |

OTHER PUBLICATIONS

Kerry, TAME: Technology Merits, Hydrocarbon Processing, May, 1992.

Primary Examiner—Asok Pal
Assistant Examiner—Bekir L. Yildirim
Attorney, Agent, or Firm—A. J. McKillop; M. D. Keen

[57] ABSTRACT

A process is disclosed for the production of alkyl tertiary alkyl ethers in $C_4+$ hydrocarbon streams rich in isoolefins, typically containing catalyst deactivating amounts of dienes and/or compounds containing heteroatoms. The process is especially advantageous in extending the cycle length for the zeolite catalyzed etherification of isoolefins in $C_4+$ FCC gasoline by reducing catalyst aging. It has been discovered that if hydrogen is cofed with the alkanol and $C_4+$ isoolefin rich feedstreams to an etherification reaction catalyzed by acidic zeolite wherein the zeolite has been impregnated with a noble metal the rate of catalyst aging or deactivation is substantially lowered. The process is especially effective, i.e., catalyst aging is particularly reduced, when hydrogen is cofed to an etherification reaction using acidic zeolite Beta catalyst containing palladium.

6 Claims, 3 Drawing Sheets

FCC GASOLINE ETHERIFICATION WITH ZEOLITE BETA CATALYST

FCC GASOLINE ETHERIFICATION OVER PD/ZEOLITE BETA CATALYST

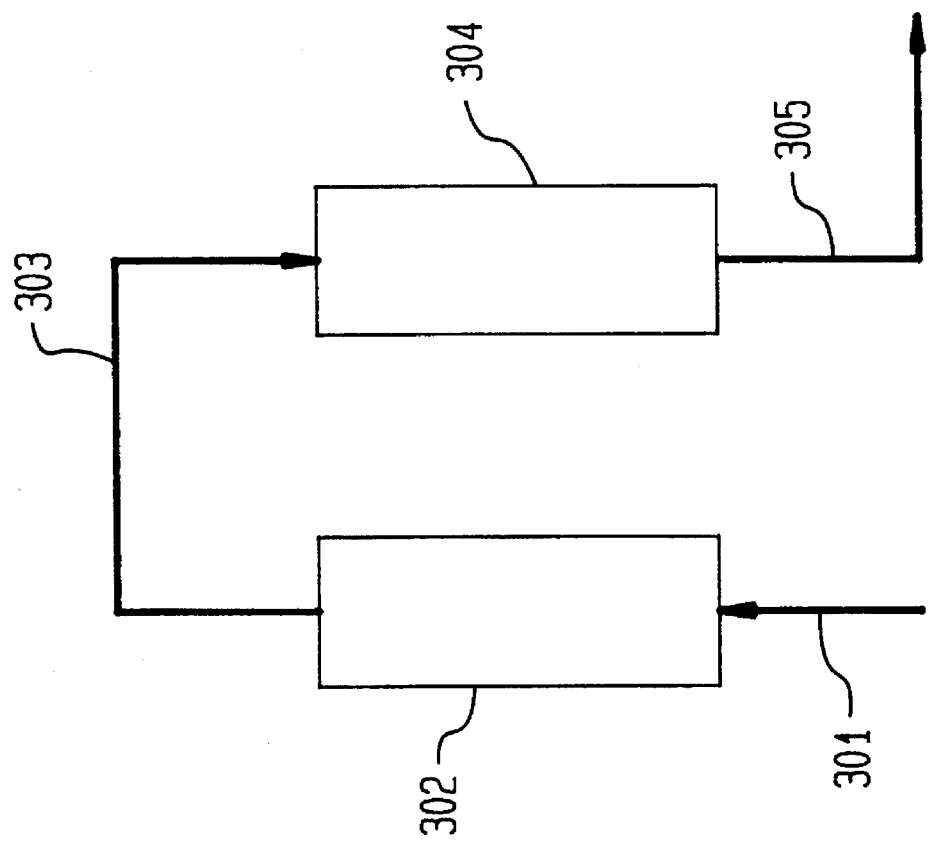

PROCESS FOR THE PRODUCTION OF TERTIARY ALKYL ETHER RICH FCC GASOLINE

This is a continuation of pending application Ser. No. 07/896,072, filed on Jun. 2, 1992, abandoned.

This invention relates to a process for increasing the oxygen content of $C_5+$ olefinic gasoline by the conversion of the isoolefin components of gasoline to high octane value alkyl tertiary alkyl ethers. The invention particularly relates to an etherification process for the production of these tertiary alkyl ethers which uses a noble metal modified regenerable acidic zeolite catalyst concurrently with cofed hydrogen. The combination of zeolite catalyst modification and hydrogen cofeeding in the etherification step results in a highly advantageous decrease in the rate of catalyst deactivation while enhancing the octane value of the gasoline.

BACKGROUND OF THE INVENTION

It is known that isobutylene and isoamylenes, and other isoalkenes or iso-olefins, produced by hydrocarbon cracking may be reacted with methanol and other $C_1$–$C_4$ lower aliphatic alcohols, or alkanol, over an acidic catalyst to provide methyl tertiary butyl ether (MTBE) or the like. Generally, it is known that asymmetrical ethers having the formula $(CH_3)_3C$—O—R, where R is a $C_1$–$C_4$ alkyl radical, are particularly useful as octane improvers for liquid fuels, especially gasoline.

MTBE, ethyl t-butyl ether (ETBE), tert-amyl methyl ether (TAME) and isopropyl t-butyl ether (IPTBE) are known to be high octane ethers. The article by J. D. Chase, et al., *Oil and Gas Journal*, Apr. 9, 1979, discusses the advantages one can achieve by using such materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

The liquid phase reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149–152, discusses the technology. Preferred catalysts are polymeric sulfonic acid exchange resin such as Amberlyst 15 and zeolites such as zeolite Beta and ZSM-5. The acid resin catalysts are effective catalysts at temperatures below 90° C. At higher temperatures the resin catalyst is unstable. Typically, with acid resin catalyst the etherification reaction is carried out in liquid phase. However, mixed phase etherification is known, particularly where the catalyst is contained as a fixed bed in a fractionator which serves to both separate the reaction products and operate as a vessel to contain the catalyst under etherification conditions. U.S. Pat. No. 4,978,807 to Smith describes an etherification catalyst reaction zone contained within a distillation tower.

Typical hydrocarbon feedstock materials for etherification reactions include olefinic streams, such as cracking process light gas containing butene isomers in mixture with substantial amounts of paraffins including n-butane and isobutane. The $C_4$ components usually contain a major amount of unsaturated compounds, such as 10–40% isobutylene, 20–55% linear butenes, and small amounts of butadiene. Also, $C_4+$ heavier olefinic hydrocarbon streams may be used, particularly mixtures of isobutylene and isoamylene. $C_5+$ olefinic hydrocarbon streams containing isoamylene comprising fluid catalytic cracking (FCC) gasoline are an especially important feedstock.

Improvements in the etherification of isoamylenes to TAME in $C_5+$ FCC gasoline are very desirable to meet the amended requirements of the Clean Air Act with respect to gasoline oxygen content while avoiding $C_4-$ hydrocarbon evaporative emissions. These amendments specify that gasoline sold in CO nonattainment areas during winter months will have 2.7 wt. % oxygen by 1992 while in ozone nonattainment areas 2.0 wt. % year round must be achieved by 1995.

As noted above, the use of zeolite catalyst for the etherification reaction of lower alkanol with isoolefins to produce MTBE and/or TAME is well known in the art. Among the advantages in employing acidic zeolite for the catalysis of etherification is the fact that it is much more readily regenerable than acidic resin catalyst. While sulfonated resin catalyst such as Amberlyst-15 are highly effective as etherification catalysts the fact that they are organic resins limits the temperatures to which they can be exposed without degradation. Zeolites, on the other hand, are stable at high temperatures which allows the repeated regeneration of deactivated catalyst. High temperature catalyst regeneration is by far the preferred route for regeneration to remove carbonaceous deposits, particularly produced by diene contaminates in the etherification hydrocarbon feedstream.

U.S. Pat. No. 4,605,787 to Chu et al., incorporated herein by reference, describes a process for the preparation of methyl tertiary butyl ether which comprises reacting isobutylene and methanol in the vapor phase in the presence of zeolite catalyst. Under the conditions described for the vapor phase etherification, side reactions, particularly the dimerization of isobutylene, are virtually eliminated.

European Patent application 0055045 to Daniels also teaches a process for the production of methyl tertiary butyl ether employing zeolite catalyst such as zeolite beta which may contain noble metals.

U.S. Pat. No. 4,330,679 to Kohler describes a process for the preparation of alkyl tertiary alkyl ethers using catalyst acidic resin which may contain a metal of subgroups VI, VII, or VII of the Periodic Table. The catalyst employed is effective in etherification without noticeable oligomerization of the olefin.

The foregoing patents, while describing etherification catalysts comprising zeolite or zeolite impregnated with noble metal or acidic resin catalyst impregnated with noble metal do not specifically teach the method of the instant invention as described hereinafter.

It is an object of the present invention to provide a process for the production of alkyl tertiary alkyl ether from $C_4$–$C_5+$ hydrocarbons with a reduced rate of catalyst deactivation and a consequent increase in cycle length before regeneration is required.

It is another object of the present invention to provide a process for the production of $C_5+$ gasoline rich in TAME employing a process and catalyst system which substantially reduces the rate of catalyst deactivation caused by the presence of dienes in the etherification feedstock.

Yet another object of the present invention is to provide a process for extending the effective life of zeolite catalyst in the production of alkyl tertiary alkyl ethers by incorporating noble metals in the catalyst and cofeeding hydrogen during the etherification reaction.

SUMMARY OF THE INVENTION

An improved process has been discovered for the production of alkyl tertiary alkyl ethers in $C_4$–$C_5$+ hydrocarbon streams rich in isoolefins, typically containing catalyst deactivating amounts of dienes and/or compounds containing heteroatoms. The process is especially advantageous in extending the cycle length for the zeolite catalyzed etherification of isoolefins in $C_5$+ FCC gasoline by reducing catalyst aging. It has been discovered that if hydrogen is cofed with the alkanol and $C_4$–$C_5$+ isoolefin rich feedstreams to an etherification reaction catalyzed by acidic zeolite wherein the zeolite has been impregnated with a noble metal the rate of catalyst aging or deactivation is substantially lowered. The process is especially effective, i.e., catalyst aging is particularly reduced, when hydrogen is cofed to an etherification reaction using acidic zeolite Beta catalyst containing palladium.

It has also been discovered that the process of the invention results in an advantageous isomerization of monoolefins, especially alpha olefins, in the feedstream to produce more useful internal olefins.

More particularly, a process for the production of high octane value alkyl tertiary alkyl ether with a reduced rate of catalyst deactivation has been discovered which comprises contacting a feedstream comprising $C_4$+ hydrocarbons rich in isoolefins and containing dienes and/or heteroatoms, an alkanol feedstream and a cofed hydrogen feedstream with regenerable, acidic metallosilicate catalyst particles, preferably aluminosilicate, containing a metal selected from Group VIIIA of the Periodic Table of the Elements, in an etherification zone under etherification conditions. An effluent stream is produced containing alkyl tertiary alkyl ether, unconverted isoolefin and unconverted alkanol; and the rate of catalyst deactivation is reduced.

In a preferred embodiment the feedstream comprises $C_5$+ hydrocarbons rich in isoolefins and containing dienes and/or alpha olefins, an alkanol feedstream and a cofed hydrogen feedstream, whereby gasoline rich in TAME is produced.

DESCRIPTION OF THE FIGURES

FIG. 3 is a schematic drawing of a two stage process of the invention employing zeolite and acidic resin catalyst.

DETAILED DESCRIPTION OF THE INVENTION

Figure 1:
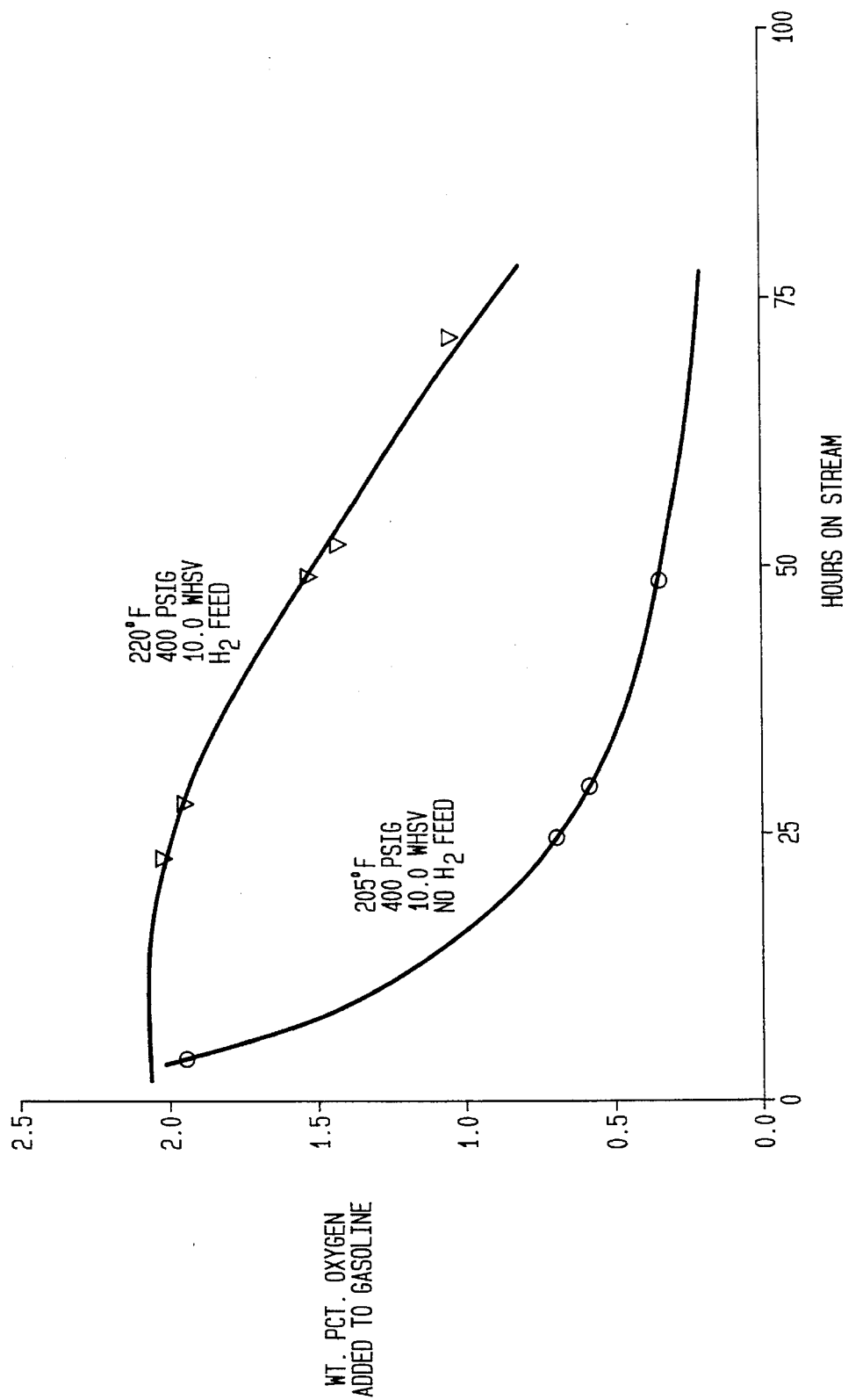
FIG. 1 is a graphical representation of the catalyst aging rate in etherification for a preferred catalyst of the invention with and without hydrogen cofeed.

Isoolefins or isoalkenes in this invention are those having the formula $R_2C=CH_2$ or $R_2C=CHR$, particularly $C_4$–$C_7$ isoolefins. Alkanols which may be used in the present invention include methanol, ethanol, 1-propanol, isopropanol, 1-butanol and 2-butanol. Anhydrous methanol is a preferred alkanol. The term lower alkyl refers to $C_1$–$C_4$ alkyl including methyl, ethyl, n-propyl and isopropyl.

In the etherification process it is known that alkanol and iso-olefins may be reacted in equimolar quantities or either reactant may be in molar excess to influence the complete conversion of the other reactant. Because etherification is an incomplete reaction the etherification effluent comprises unreacted alkanol and unreacted hydrocarbons. On a stoichiometric equivalency basis, equimolar quantities of methanol and iso-olefins are advantageous but an excess between 2 and 200% of either component can be passed to the etherification reaction unit. In the present invention, the molar ratio of alkanol to iso-olefin, such as methanol to iso-butylene, can be between 0.7 and 2, but preferably the molar ratio is 1 for methanol to isobutylene in liquid phase etherification. Advantageously, the excess methanol may be about 40% or more when the hydrocarbon feedstream comprises significant quantity of isoamylenes, but equimolar quantities are preferred when the hydrocarbon feedstream iso-olefin component consists essentially of $C_4$ hydrocarbons.

FCC gasoline is a preferred hydrocarbon feedstock for the process of this invention, although isoolefin rich $C_4$ or $C_4$+ hydrocarbon streams can be used. Typically, FCC gasoline comprises predominantly $C_5$–$C_7$ hydrocarbons containing about 25% etherifiable isoolefins, particularly isoamylenes. Dienes in small quantities (<1%) are also present in FCC gasoline and are known to contribute to catalyst deactivation in prior art etherification processes. Small quantities of alpha olefins may also be present. The feedstream also contains traces of heteroatoms such as nitrogen and sulfur in quantities sufficient to influence the rate of catalyst aging.

The catalysts useful in the etherification process of the invention as described herein contain a zeolite sometimes referred to as medium pore or ZSM-5 type. It is preferred to use a medium pore shape selective acidic metallosilicate zeolite selected from the group consisting of ZSM-5, ZSM-11, ZSM-12, ZSM-22, ZSM-23, ZSM-35, ZSM-50, MCM-22, as well as larger pore zeolite Y and zeolite Beta, as the zeolite component of the catalyst used in the process of this invention. Acidic zeolite Beta is the preferred zeolite. ZSM-5 is more particularly described in U.S. Reissue Pat. No. 28,341 (of original U.S. Pat. No. 3,702,886), the entire contents of which are incorporated herein by reference.

ZSM-11 is more particularly described in U.S. Pat. No. 3,709,979, the entire contents of which are incorporated herein by reference.

Zeolite ZSM-12 is described in U.S. Pat. No. 3,832,449, to which reference is made for the details of this catalyst.

ZSM-22 is more particularly described in U.S. Pat. No. 4,046,859, the entire contents of which is incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

Zeolite ZSM-50 is described in U.S. Pat. No. 4,640,829, to which reference is made for details of this catalyst.

Zeolite Beta is described in U.S. Reissue Pat. No. 28,341 (of original U.S. Pat. No. 3,308,069), to which reference is made for details of this catalyst.

MCM-22 is more particularly described in U.S. Pat. No. 4,954,325, the entire contents of which are incorporated herein by reference.

Zeolite Y is described in U.S. Pat. No. 3,130,007, to which reference is made for details of this catalyst.

The original cations associated with zeolites utilized herein can be replaced by a wide variety of other cations according to techniques well known in the art, e.g., by ionexchange. Typical replacing cations include hydrogen, ammonium, alkyl ammonium and metal cations, and their mixtures. Metal cations can also be introduced into the zeolite. In the case of metal cations, particular preference is given to metals of Groups IB to VIIIA of the Periodic Table, including, by way of example, iron, nickel, cobalt, copper, zinc, palladium, calcium, chromium, tungsten, molybdenum, rare earth metals, etc. These metals can also be present in the form of their oxides.

A typical ion-exchange technique involves contacting the particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249; 3,140,251; and 3,140,253.

Following contact with a solution of the desired replacing cation, the zeolite is then preferably washed with water and dried at a temperature ranging from about 150° to about 600° F. and thereafter calcined in air or other inert gas at temperatures ranging from about 500° to about 1500° F. for periods of time ranging from about 1 to about 48 hours or more.

For incorporation into zeolite useful in the instant invention metals of Group VIIIA of the Periodic Table of the Elements are preferred. Zirconia-bound zeolite Beta containing palladium (about 0.3%) and having a high alpha value (about 400) is a particularly preferred catalyst for the novel etherification process of the instant invention. Alpha value, or alpha number, is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980).

It has been discovered that the method of incorporating palladium in zeolite catalyst of the invention can result in catalysts having widely varying etherification activity. To illustrate this discovery, two methods are described, Examples A and B, to introduce palladium into commercially available zeolite Beta catalyst. According to the etherification activity test described in Example C, catalyst A has an etherification activity of 0.021 grams converted per gram of catalyst per hour while the activity of catalyst B is 0.004 grams converted per gram of catalyst per hour. The method for impregnating zeolite Beta catalyst with palladium described in Example A is preferred for the process of this invention.

Example A

A physical mixture of 70 parts zeolite Beta, 24 parts zirconium oxide and 30 parts AZC (Magesium Elektron Ammonium Zirconium Carbonate 20% $ZrO_2$) was mulled to form a uniform mixture. Sufficient amount of deionized water (DI) was added to form an extrudable paste. The mixture was auger extruded to $1/16$" quadrulobe shaped extrudates and dried in an oven at 120° C. The extrudates were then nitrogen calcined at 480° C. for 3 hours followed by a 6 hour calcination at 538° C. The extrudates were first humidified and then immersed in a circulating aqueous solution (4cc/g catalyst). Then 0.069 M palladium tetraamine (II) chloride solution (1cc/g catalyst) was added to the aqueous solution over a four hour period. After eight hours of circulation the extrudates were dried in a 120° C. oven. The dried extrudates were air calcined for 2 hours at 288° C. and four 3 hours at 350° C. The finished palladium/Beta/$ZrO_2$ catalyst had 0.30 wt. % Pd.

Example B

A physical mixture of 70 parts zeolite Beta, 24 parts zirconium oxide and 30 parts AZC (Magesium Elektron Ammonium Zirconium Carbonate 20% $ZrO_2$) was mulled to form a uniform mixture. Sufficient amount of deionized water (DI) was added to form an extrudable paste. The mixture was auger extruded to $1/16$" extrudates and dried in an oven at 120° C. The extrudates were then nitrogen calcined at 480° C. for 3 hours followed by a 6 hour air calcination at 538° C. The extrudates were first humidified and than immersed in a circulating 0.2 M $NH_4NO_3$ solution (3.5 cc/g catalyst). Then 0.62 M palladium tetraamine (II) chloride solution was added to the $NH_4NO_3$ solution over a four hour period. After eight hours of circulation, the extrudates were washed with DI water and dried in an oven at 120° C. The extrudates were air calcined for three hours at 288° C. The finished palladium/Beta/$ZrO_2$ catalyst had 0.32 wt. % Pd.

Example C

Etherification Activity Test Procedure

Etherification activity is conducted in a 150 cc autoclave using 6.54 grams of crushed Pd/zeolite Beta/$ZrO_2$ and a solution consisting of 2-methyl-1-pentene (25.2 grams), n-hexane (25.8 grams), and absolute methanol (14.4 grams). The reactor is heated to 180° F. at 50 psig over 15 minutes. Two hours after the initiation of heating, samples of the liquid within the reactor are obtained and analyzed by gas chromatography. The etherification activity of the catalyst is taken to be grams of converted (to $C_6$ methyl ether) per gram of catalyst per hour.

The process of the invention involves the discovery that cofeeding hydrogen to an isoolefin etherification reaction, especially one using FCC feedstream and employing regenerable acidic zeolite catalyst particles containing palladium or other Group VIII metal, provides the following advantages: a reduced rate of catalyst deactivation or aging; isomerization of alpha olefins to more useful internal olefins; reduction in diene content; and an enhancement in the ease of catalyst reactivation with hydrogen.

The effectiveness of hydrogen co-feeding for decreasing the aging rate of acidic zeolite Beta catalyst containing palladium and enhancing desirable side reactions was demonstrated in an accelerated aging test. As shown in FIG. 1, the catalyst activity, measured as the amount of oxygen incorporated into FCC gasoline through the formation of methyl ethers, remained higher when hydrogen was added to the feedstream. Also, the use of hydrogen co-feed promoted desirable side reactions such as olefin isomerization as shown in Table 1. These desirable side reactions increase the extent of oxygen incorporation into the gasoline. Diene removal also reduces gum formation in the hydrocarbon product.

The following Examples illustrate the process of the present invention and the effect of that process on catalyst aging.

Example 1

The etherification of FCC gasoline is performed in a fixed bed reactor. In a ¼" I.D. stainless steel reactor, four grams of palladium impregnated acidic zeolite Beta catalyst particles (20/60 mesh) is mixed with 30 vol. % sand (60/120 mesh), and heated to 400° F. (205° C.) at 400 psig (2800 kPa) under hydrogen and maintained under these conditions for 16 hours, after which time the temperature is decreased to 200° F. (93° C.). The hydrocarbon feed comprising $C_5$-215° F. (102° C.) FCC gasoline is blended with absolute methanol in a three to one ratio (75 wt. % hydrocarbon/25 wt. % alcohol). For the case of only liquid feed, which is performed in a downflow reactor, the reaction is commenced by stopping the hydrogen flow and feeding the FCC gasoline/methanol blend to the reactor at a rate of 10.0 grams of liquid per gram of catalyst per hour. The mixed liquid/hydrogen experiment is run upflow, using the same liquid feed rate and 5 cc/minute gas feed rate. In both cases, the total liquid product is contacted with water to remove unreacted methanol from the hydrocarbons.

Example 2

Figure 2:
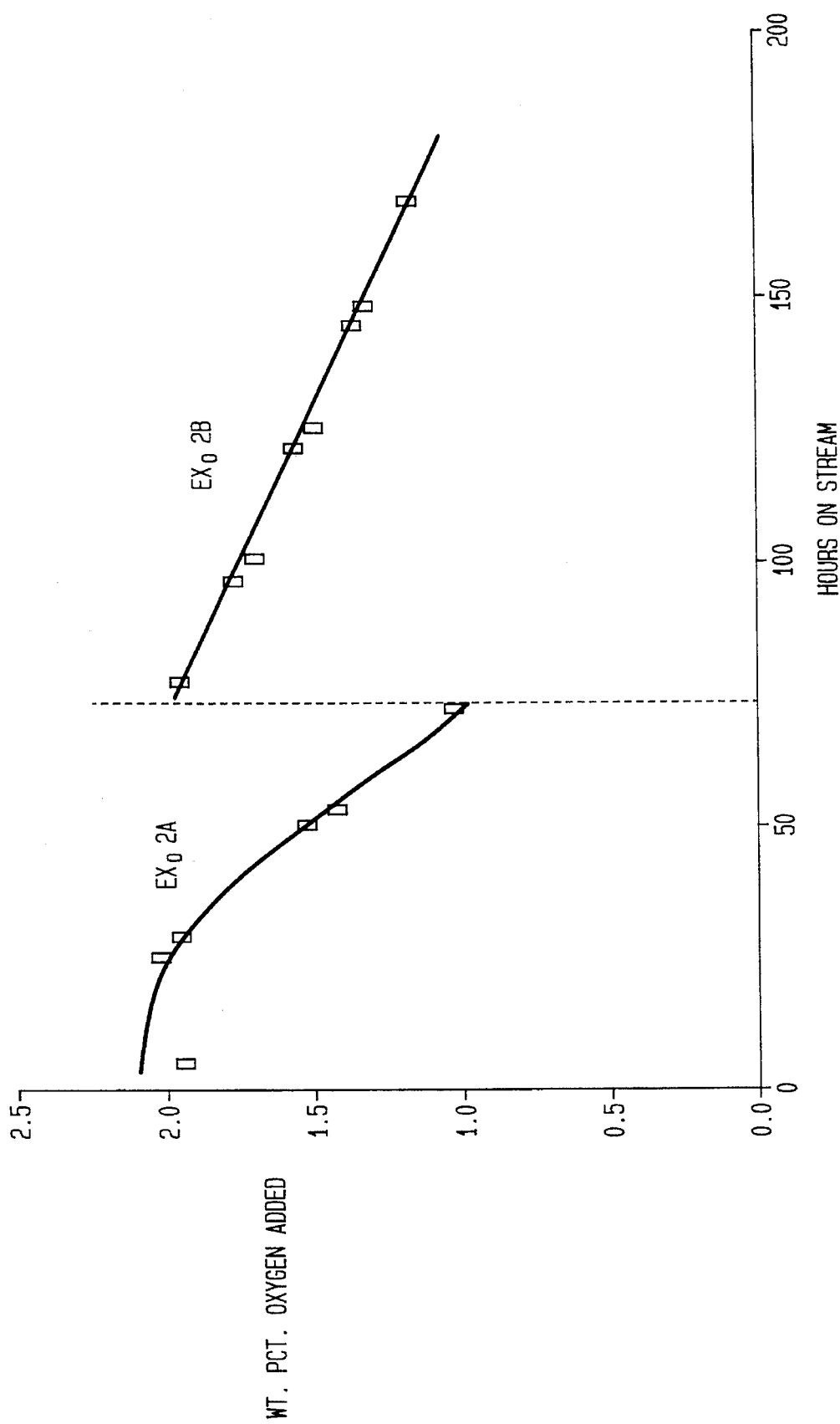
FIG. 2 is graphical representation comparing the etherification process of the invention under different process conditions.

As shown by the results of this Example, the rate of hydrogen addition during etherification can affect the catalytic performance of the Pd/zeolite Beta catalyst. Following in-situ treatment of the catalyst with hydrogen at 750° F. (399° C.) for 72 hours to restore its initial activity after etherification according to the process of Example 1, the catalyst is evaluated under etherification conditions at higher overall pressure and higher hydrogen flow rate. As shown in FIG. 2 the rate of deactivation decreased at these new conditions. Example 2A etherification conditions were 220° F. reaction temperature at 400 psig and 5cc/minute hydrogen feed; Example 2B etherification conditions were 220° F. reaction temperature at 600 psig and 10 cc/minute hydrogen feed. The extent of pentene isomerization is also increased by the different operating parameters as shown in Table 1.

TABLE 1

Effect of Hydrogen Co-feed on Hydroisomerization of Linear Pentenes During FCC Etherification Over Pd/Zeolite Beta

| Example | Feed | 2C | 2D | 2E |
|---|---|---|---|---|
| Reaction Conditions | | | | |
| Temperature (°F.) | — | 206 | 224 | 233 |
| Pressure (psig) | — | 400 | 400 | 600 |
| Liquid Feed (WHSV) | — | 10.0 | 10.0 | 10.0 |
| Hydrogen Feed (SCCM) | — | 0 | 5.0 | 10.0 |
| Linear Pentene Dist. | | | | |
| 1-Pentene | 17.5 | 17.4 | 5.0 | 4.7 |
| cis-2-pentene | 29.9 | 29.8 | 70.0 | 71.5 |
| trans-2-pentene | 52.5 | 52.7 | 25.0 | 23.8 |

Since terminal linear olefins tend to have lower octane values than internal olefins, reducing the concentration of terminal olefins as depicted in Table 1 for the invention is highly advantageous and, along with the elimination of dienes, provides benefits in downstream alkylation.

As shown in Table 2, methanol etherification of branched olefins in light FCC gasoline carried out by the process of the invention increases the oxygen content of the hydrocarbon to 1.9 wt. %, significantly lowers the bromine and reduces Reid vapor pressure with no change in (R+M)/2 octane value.

TABLE 2

Effect of Etherification on FCC Gasoline Properties

| | Treated Feedstock | Etherified Product |
|---|---|---|
| Oxygen Content, Wt % | 0.0 | 1.9 |
| TAME, wt % | 0.0 | 5.8 |
| $C_6$ Methyl Ethers, Wt % | 0.0 | 5.4 |
| $C_7$ Methyl Ethers, Wt % | 0.0 | 2.0 |
| Bromine Number | 85 | 69 |
| RVP (psi) | 7.0 | 6.3 |
| (R + M)/2 | 86.2 | 86.1 |

Although single-pass fixed bed reactors are used in the foregoing Examples of the process of the invention, other configurations (e.g. fixed bed reactors with recycle, etc.) may be used for the process.

Referring to FIG. 3, a multi-stage process is illustrated for implementation of the process of this invention in conjunction with acid resin catalyzed etherification. Since palladium-impregnated zeolite Beta performs a number of important catalytic functions such as olefin isomerization and diene removal, multi-stage processes using this catalyst and synthetic resins provides a unique and efficacious route for upgrading olefinic feedstreams for "clean fuels" applications. In FIG. 3, a feedstream 301 comprising FCC gasoline, methanol and hydrogen is passed to etherification reactor 302 containing zeolite Beta catalyst impregnated with palladium. Etherification is carried out in this stage at moderate to high temperatures to complete the etherification reaction as well as olefin isomerization and diene saturation. The effluent from the etherification zone containing unconverted alkanol and isoolefins is passed 303 to a second etherification zone 304 containing Amberlyst-15 etherification catalyst. Etherification in this second stage reactor is carried out at a lower temperature. The effluent 305 from the reactor is passed to a debutanizer or depentanizer for product recovery of $C_5$+ gasoline rich in alkyl tertiary alkyl ethers.

The etherification conditions useful in the present invention for either $C_4$+ or $C_5$+ feedstreams containing isoalkenes, or isoolefins, include temperature between about 100° and 500° F., pressure between about 100 and 1000 psig, hydrocarbon feed rate between about 0.1 and 10 weight hourly space velocity (WHSV) based on catalyst, and hydrogen flow rate between about 10 and 2000 SCF/Bbl. Preferably, the etherification conditions comprise temperature of about 150°– 400° F., pressure of about 200–600 psig, hydrocarbon feed rate of about 0.5–5 weight hourly space velocity (WHSV) based on catalyst, and hydrogen flow rate of about 50–1000 SCF/Bbl.

Modifications, such as the use of other metals (platinum, etc.) and other catalyst binders (silica, silica-alumina, etc.) are considered within the scope of the invention to enhance the properties of the zeolite-based catalyst.

The zeolite catalyst is converted to the hydrogen form prior to use in the process of this invention. Although the process of this invention extends the active useful life of the catalyst, eventually after extended use in the process of this invention the catalyst will require regeneration to restore activity. This may be effected with hydrogen gas at elevated temperature. Optionally, the catalyst can be regenerated or reactivated oxidatively by treatment with air or oxygen to combust and remove carbonaceous deposits. Also, combinations of oxidative regeneration and regeneration by hydrogen gas can be used.

While the invention has been described by reference to specific embodiments there is no intent to limit the scope of the invention except to describe in the following claims.

What is claimed is:

1. A catalytic process for the production of $C_5+$ gasoline containing alkyl tertiary alkyl ether and a reduced amount of linear 1-alkenes at longer catalyst life comprising:

contacting a feedstream comprising $C_5+$ hydrocarbons rich in isoolefins and containing dienes and linear 1-alkenes, an alkanol feedstream and a cofed hydrogen feedstream with a acidic catalyst particles containing zeolite beta and a Group VIIIA metal component in an etherification zone under etherification conditions whereby said isoolefins are converted to said ether, said linear 1-alkenes are converted to higher octane value internal olefins and said dienes are hydrogenated to produce an effluent stream comprising said gasoline at a reduced rate of catalyst deactivation.

2. The process of claim 1 wherein said catalyst comprises palladium impregnated zeolite Beta.

3. The process of claim 2 wherein said catalyst comprises zirconia-bound palladium zeolite Beta containing about 0.3 weight percent palladium having an alpha value of about 400.

4. The process of claim 3 wherein said catalyst was prepared by a process comprising:

preparing an aqueous extrudate of zeolite Beta, zirconium oxide and zirconium carbonate;

drying and calcining the extrudate under nitrogen;

humidifying the extrudate and then immersing the extrudate in water;

treating the extrudate in water with palladium tetraamine (II) chloride solution;

drying and calcining the palladium treated extrudate.

5. The process of claim 1 in which the alkanol comprises methanol and the alkyl tertiary alkyl ether comprises methyl tertiary amyl ether.

6. The process of claim 1 in which the $C_5+$ hydrocarbon stream comprises an olefinic gasoline from a fluid catalytic cracking process.

* * * * *